(12) United States Patent
Teodorescu et al.

(10) Patent No.: US 12,250,329 B2
(45) Date of Patent: Mar. 11, 2025

(54) SYSTEMS AND METHODS FOR USING BLOCKCHAIN TO SECURE DATA ACQUIRED IN SURGICAL AND OTHER MEDICAL PROCEDURES

(71) Applicant: SURGIBOX INC., Cambridge, MA (US)

(72) Inventors: Mike Horia Mihail Teodorescu, Cambridge, MA (US); Atif Mohammad Rakin, Storrs, CT (US); Gelu Comanescu, Washington, DC (US)

(73) Assignee: SurgiBox Inc., Cambridge, MA (US)

( * ) Notice: Subject to any disclaimer, the term of this patent is extended or adjusted under 35 U.S.C. 154(b) by 221 days.

(21) Appl. No.: 17/894,115

(22) Filed: Aug. 23, 2022

(65) Prior Publication Data
US 2024/0073042 A1 Feb. 29, 2024

(51) Int. Cl.
*H04L 9/00* (2022.01)
*G06F 21/64* (2013.01)
(Continued)

(52) U.S. Cl.
CPC .............. *H04L 9/50* (2022.05); *G06F 21/64* (2013.01); *G16H 10/60* (2018.01); *G16H 50/70* (2018.01); *H04L 9/3239* (2013.01)

(58) Field of Classification Search
CPC ......... H04L 9/50; H04L 9/3239; G06F 21/64; G16H 10/60; G16H 50/70
See application file for complete search history.

(56) References Cited

U.S. PATENT DOCUMENTS 11,003,791 B2 * 5/2021 Wang ................. G16B 50/40
2019/0156923 A1 5/2019 Kain
(Continued)

FOREIGN PATENT DOCUMENTS

WO WO2018014003 A1 1/2018

OTHER PUBLICATIONS

International Search Report and Written Opinion for PCT/US2022/041266, issued on Feb. 7, 2023 (see attached).
(Continued)

*Primary Examiner* — Cheng-Feng Huang
(74) *Attorney, Agent, or Firm* — Fish & Richardson P.C.

(57) ABSTRACT

A data management system for managing data acquired during medical procedures is disclosed. The data management system may include a centralized database and/or a plurality of databases storing procedure records. Each of the procedure records comprises data acquired by a data acquisition system during a medical procedure performed on a specific patient. The data management system enables users to access, search and perform analytics on data in the databases. The system may further include a blockchain configured to render immutable the data in the centralized database and databases. The data management system may include a centralized data access system enabling users to access the plurality of databases even when each of the databases are operated by different healthcare providers and when the procedure records in the databases are owned by the different owners. The data acquisition system may be part of a portable-surgical-system for performing surgery in the field.

24 Claims, 12 Drawing Sheets

(51) Int. Cl.
*G16H 10/60* (2018.01)
*G16H 50/70* (2018.01)
*H04L 9/32* (2006.01)

(56) References Cited

U.S. PATENT DOCUMENTS

| | | | |
|---|---|---|---|
| 2020/0143084 A1 | 5/2020 | Rosenberg | |
| 2020/0146638 A1 | 5/2020 | Wagner | |
| 2020/0327250 A1* | 10/2020 | Wang | G06N 20/00 |
| 2020/0389309 A1* | 12/2020 | Ricotta | H04L 9/32 |
| 2021/0073285 A1* | 3/2021 | Hunter | G06F 16/212 |
| 2021/0098092 A1 | 4/2021 | Katuwal | |
| 2021/0117408 A1* | 4/2021 | Figueredo de Santana | G06F 16/9027 |
| 2021/0342836 A1* | 11/2021 | Cella | H04L 9/3239 |
| 2022/0131699 A1* | 4/2022 | Kimmel | H04L 63/0861 |

OTHER PUBLICATIONS

Checketts et al., "Recommendations for standards of monitoring during anaesthesia and recovery 2015: Association of Anaesthetists of Great Britain and Ireland," Anaesthesia, Jan. 2016, 71(1):85-93.
Thomas, "Intraoperative Monitoring (IOM)," News Medical Net, Feb. 27, 2019, 3 pages.
US Department of Health, "Guidance Regarding Methods for De-identification of Protected Health Information in Accordance with the Health Insurance Portability and Accountability Act (HIPAA) Privacy Rule," Nov. 26, 2012, 32 pages.

\* cited by examiner

FIG. 4

Procedure-Record

1. Surgical procedure description
2. Patient de-identified info (e.g., age, medical history)
3. Intracranial pressure-data
4. Blood-pressure-data
5. X-ray images, MRI-images
6. Surgery Videos
7. Voiceover data
8. Textual inputs
   ...

25

SYSTEMS AND METHODS FOR USING BLOCKCHAIN TO SECURE DATA ACQUIRED IN SURGICAL AND OTHER MEDICAL PROCEDURES

BACKGROUND OF THE INVENTION

I. Field of the Invention

Exemplary embodiments of the present invention relate to systems and methods for securing data acquired during surgical and other medical procedures.

II. Discussion of the Background

Surgical procedures and other medical procedures involve the monitoring of many physiological functions of the patient and the monitoring of various parameters of the environment in which the procedure is performed. The very fast pace of technological advances in areas such as sensing and imaging technologies is likely to bring a significant increase in the monitored functions, number of parameters, precision of the measurements, and the amount of data generated and recorded by patient monitoring during surgical and other medical procedures.

A patient undergoing a medical procedure, such as surgery under anesthesia, is usually experiencing a number of unusual patterns of behavior with regard to the normal functioning of various body systems. In other words, various body systems function under unusual and potentially dangerous conditions. This creates the need for monitoring and determining patient's physiological status essentially on a continuous basis. The types of sensors, equipment and monitoring required vary with the procedure being undertaken and the patient. The sensors and equipment used to monitor a patient throughout a surgical operation may be made of one single system that can be set to accurately and continuously measure a set of patient parameters that reflect the functioning of the body systems. Alternatively, multiple monitoring systems mat be employed. Various sensors, electrodes, and imaging systems may be attached to the patient or positioned such as to acquire the desired information. The results of these measurements may be displayed on monitors and saved as data files in various databases on on-site computers or on remote data storage facilities.

Example of measurements and parameters monitored in surgical procedures include: heart's electrical activity (via electrocardiograms); respiratory rate; blood pressure; body temperature (using temperature probes or thermometers); the cardiac output; the arterial blood oxygen level measured by a pulse oximeter (e.g., employing a photoelectric sensor attached to a finger); venous oxygenation; pulmonary functions such as end-tidal carbon dioxide; arterial pH; neurophysiological monitoring, etc. For example, intracranial pressure may be monitored in patients suffering from head trauma, patients having a high intracranial pressure because of brain tumors, patients suffering intracranial hemorrhage, or patients with edema. In such a case, the intracranial pressure may be measured via a sensor inserted through a hole made in the skull with the purpose of detecting rises in the pressure inside the head and with the purpose of recording the evolution in time of the measured parameters (see e.g., Intraoperative Monitoring; by Dr. Liji Thomas, MD, News Medical Net (Feb. 27, 2019)). The importance of employing reliable and precise methods and devices of monitoring patients during surgery cannot be overstated. For example, as it is well known the core human body temperature needs to be maintained in a narrow range because all body tissues function optimally within a narrow range of temperatures. The core body temperature is somewhat different from the skin temperature since skin temperature is highly dependent on other factors such as the ambient heat exposure. Thus, there is a need for precise monitoring of core body temperature. Thermistors, thermocouples, and infrared thermometers, are the generally used to measure near-core temperature within 0.5 degrees.

Medical regulatory authorities in most countries have established standards and procedures for ensuring the quality of patient monitoring during surgery, such as a minimum of monitoring procedures and devices which need to be employed during surgery, anesthesia, and recovery (see for example "Recommendations for standards of monitoring during anesthesia and recovery 2015", Association of Anesthetists of Great Britain and Ireland).

A large amount of valuable patient monitoring data is acquired during medical procedures from many types of sensors and imaging equipment. Such data can be highly valuable because data analytics on it can provide important medical insights which are likely to lead to medical discoveries and significant improvements of medical procedures. More data acquired from more patients during more procedures is likely to lead to more discoveries and more improvements in safety and effectiveness of current medical procedures as well as designing novel medical procedures. For brevity and consistence hereinafter we may refer to the data acquired while monitoring a patient during a medical procedure as "medical-procedure-data" or "procedure-data". However, the operators are not always saving/storing for future use such medical procedure data. Even when stored, medical procedure data is not properly protected and is vulnerable to breaches which may lead to patient's loss of privacy and to liabilities for the healthcare provider. Thus, there is a need for systems and methods for acquiring data generated in medical procedures. There is also a need for saving and securing the medical-procedure-data so as to prevent data breaches, to ensure data-integrity (preventing data alterations and falsification), and to protect against data loss. Blockchain technology has been often mentioned as providing the state of the art when it comes to securing the integrity of data.

Moreover, medical procedure data acquired by one party (e.g., a hospital) is most often not shared with others, is not accessible by researchers from other institutions, and is generally not made accessible to the public for use. The reasons for this are primarily related to the need to protect "patient privacy" and to legal liability issues. Health information such as medical-procedure-data can be de-identified (see for example "Guidance Regarding Methods for De-identification of Protected Health Information in Accordance with the Health Insurance Portability and Accountability Act (HIPAA) Privacy Rule" published by the U.S. Department of Health and Human Services). In some instances, healthcare institutions (e.g. hospitals, private practices) may share de-identified medical data with others and may make it available for data analytics and research by other institutions. However, there is no centralized database or centralized way to access medical procedure data acquired by the large number of institutions acquiring such data. Furthermore, there is currently no system to access all de-identified procedure data across all medical record systems in the United States.

Thus, there is a need for systems and methods enabling easy access to medical-procedure-data generated by healthcare service providers regardless of location and medical records system, so as to allow scientists to perform data analytics, research and scientific studies on the data. There is also a need for systems and methods for aggregating the data into centralized systems (e.g., databases) which can be accessed and used in various scientific studies.

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

SUMMARY OF THE INVENTION

Exemplary embodiments of the present invention provide a data-management-system for managing data acquired during medical procedures. The data-management-system may include a centralized-database storing a plurality of procedure-records. Each of the procedure-records comprises data acquired by a data-acquisition-system during a medical procedure performed on a specific patient. The data-management-system may further include a user-access-module configured to enable users to access data in the centralized-database and a search-module configured to enable users to perform searches on data in the centralized-database. The data-management-system may further include a data-analytics-module configured to enables users to perform data-analytics and scientific studies on the data in the centralized-database.

The centralized-database is connected with a plurality of data-acquisition-systems. Each of the data-acquisition-systems may include sensors attached to a patient and monitoring physiological parameters of the patient. The data-acquisition systems may further include an operator-input-module configured to receive information from an operator regarding the medical procedure to be performed and information about the patient. The data-acquisition systems may further include a data-acquisition-module configured to receive data from the sensors and to form a procedure-data-structure comprising the data from the sensors. The data-acquisition systems may further include a de-identification-module configured to form a de-identified-procedure-data-structure. The data-management-system may further include a record-generating-module configured to receive de-identified-procedure-data-structures and to form corresponding procedure-records comprising the de-identified-procedure-data-structure.

The data-management-system may further include a blockchain system configured to render immutable the data in the procedure-records and the centralized-database. The blockchain system may store datasets, or copies of datasets, of the centralized-database. The blockchain system may include a hash-module configured to calculate hash values for one or more datasets comprised by the procedure-records and to store the hash values on the blockchain as block-hashes. The data-management-system may further include a data-verification-module configured to verify, for each of the datasets of the procedure-records, the integrity of the dataset by calculating a hash of the dataset and comparing the calculated hash with the corresponding block-hash previously stored on the blockchain.

The data-management-system may further include a classification-module configured to classify the procedure-records in the centralized-database function of one or more classification-parameters and to form a plurality of data-classes corresponding to a classification-parameter.

In another exemplary embodiment the data-management-system may include a centralized-data-access-system. The centralized-data-access-system may include a database-access-module configured to connect the centralized-data-access-system with a plurality of databases. Each of the databases may include a plurality of procedure-records. Each of the databases is connected to a plurality of data-acquisition-systems such as the ones described above. Each of the procedure-records comprises de-identified information about a medical procedure performed on a patient. The data-management-system may further include an user-interface-module configured to enable users to access data-files in the databases and a search-module configured to enable the users to search data in the databases. The data-management-system may further include a data-analytics-module configured to enable users to perform data-analytics and scientific studies on data in the databases. Each of the databases may be owned by a different healthcare service-provider (e.g. hospital, private practice). The data-management-system may further include a classification-module and a blockchain system configured to render immutable the data in the databases.

In an exemplary embodiment a data-acquisition-system is part of a portable-surgical-system configured to be used for performing surgical procedures in one or more of the following environments: in the field, outdoors, tents, cottages, residential rooms, and environments other than operating rooms.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

FIG. 4 shows an exemplary embodiment of a procedure-record for a medical procedure performed on a patient.

DETAILED DESCRIPTION

Figure 1:
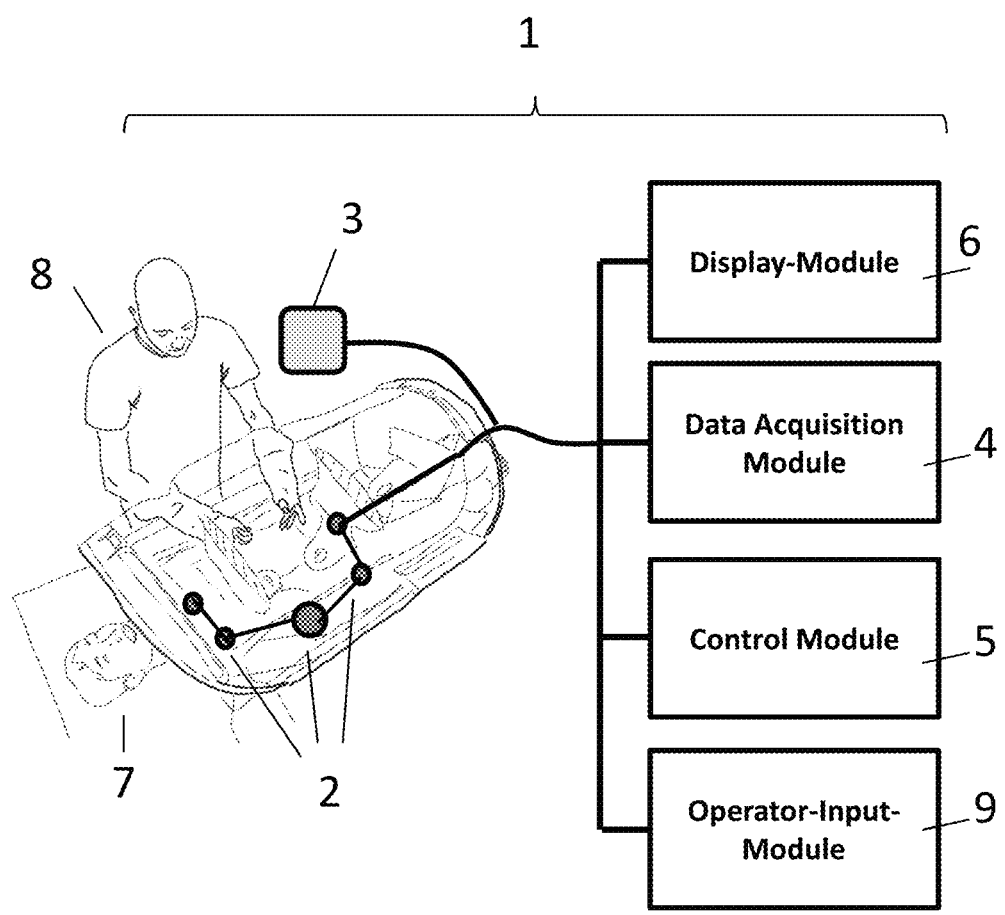
FIG. 1 shows an exemplary embodiment of a data-acquisition-system configured to acquire data generated during a surgical or other medical procedure performed on a patient by one or more medical-operators.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure is thorough, and will fully convey the scope of the invention to those skilled in the art. Like reference numerals in the drawings denote like elements.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

FIG. 1 shows an exemplary embodiment of a data-acquisition-system 1. The data-acquisition-system is configured to acquire data generated during surgical and/or other medical procedures performed on a patient 7 by one or more medical-operators 8 (e.g., surgeons, anesthesiologists, nurses). A medical service-provider may own and control the data generated during the medical-procedure and acquired by the data-acquisition-system. In an alternate embodiment, a medical service provider will not create identifiable data, or a de-identified copy of the data will be generated, in which case the data will be transmitted directly by the data-acquisition-system to a data-management system 10.

The data-acquisition-system may include a plurality of sensors 2, one or more imaging devices 3, a data acquisition module 4, a controller module 5, a display module 6, an operator-input-module 9, and/or a de-identification-module. During a medical procedure, such as a surgery, data may be acquired by various sensors, electrodes, and imaging systems. The sensors, electrodes, and imaging systems may be attached to the patient or positioned such as to acquire the desired information. The results of these measurements may be displayed on computer monitors and displays 6. The data may be saved as data files on various on-site computers or on remote data storage facilities.

The one or more sensors may include one or more of the following: sensors configured to measure one or more temperatures at various places on or inside the body of the patient; sensors for acquiring information about the heart's electrical activity (e.g., electrocardiograms); sensors measuring a respiratory rate; blood pressure sensors; sensors measuring cardiac output; sensors measuring arterial blood oxygen level such as pulse oximeters; sensors measuring venous oxygenation; sensors measuring pulmonary functions such as end-tidal carbon dioxide; sensors measuring arterial pH; sensors for neurophysiological monitoring; sensors for monitoring intracranial pressure in patients suffering from head trauma, or patients having a high intracranial pressure because of brain tumors, or patients having intracranial hemorrhage; sensors disposed on catheters inserted in the circulatory system (e.g., position sensors); sensors monitoring airflow, airborne oxygen content, and air temperature (e.g., ventilator systems and anesthesia delivery machines); etc. The imaging devices may include one or more visible camera configured to monitor the surgical field; cameras configured to perform imaging inside the body, such as endoscopic cameras; and IR cameras. The imaging devices may further include X-ray imaging machines; Computer Tomography (CT) imaging machines; MRI machines; PET scanners; etc. The data-acquisition-system may further include a sound-recording-device configured to record sound (e.g. discussions between medical operators) data during medical procedure.

The display-module may be a computer monitor and may be configured to show some of the data acquired by the sensors in real time. The control-module may be configured to control the sensors and imaging devices. The data acquisition module may be connected with the sensors and the imaging devices so as to receive information from the sensors and imaging devices via cable connections, Wi-Fi, Bluetooth or any other suitable connection means known by those skilled in the art. The data acquisition module may store the data on-site (e.g., computer hard drives, flash memory modules, optical memory, etc.) or on remote data storage facilities such as in the cloud or in data centers. The operator-input-module 9 may enable the operator to enter information about the patient and about the medical procedure to be performed. This data entry may be via a touchscreen where the user may be presented a set of questions and answers or categories to select from, text input via a keyboard or touchscreen, speech, or other means known by those skilled in the art.

Figure 2:
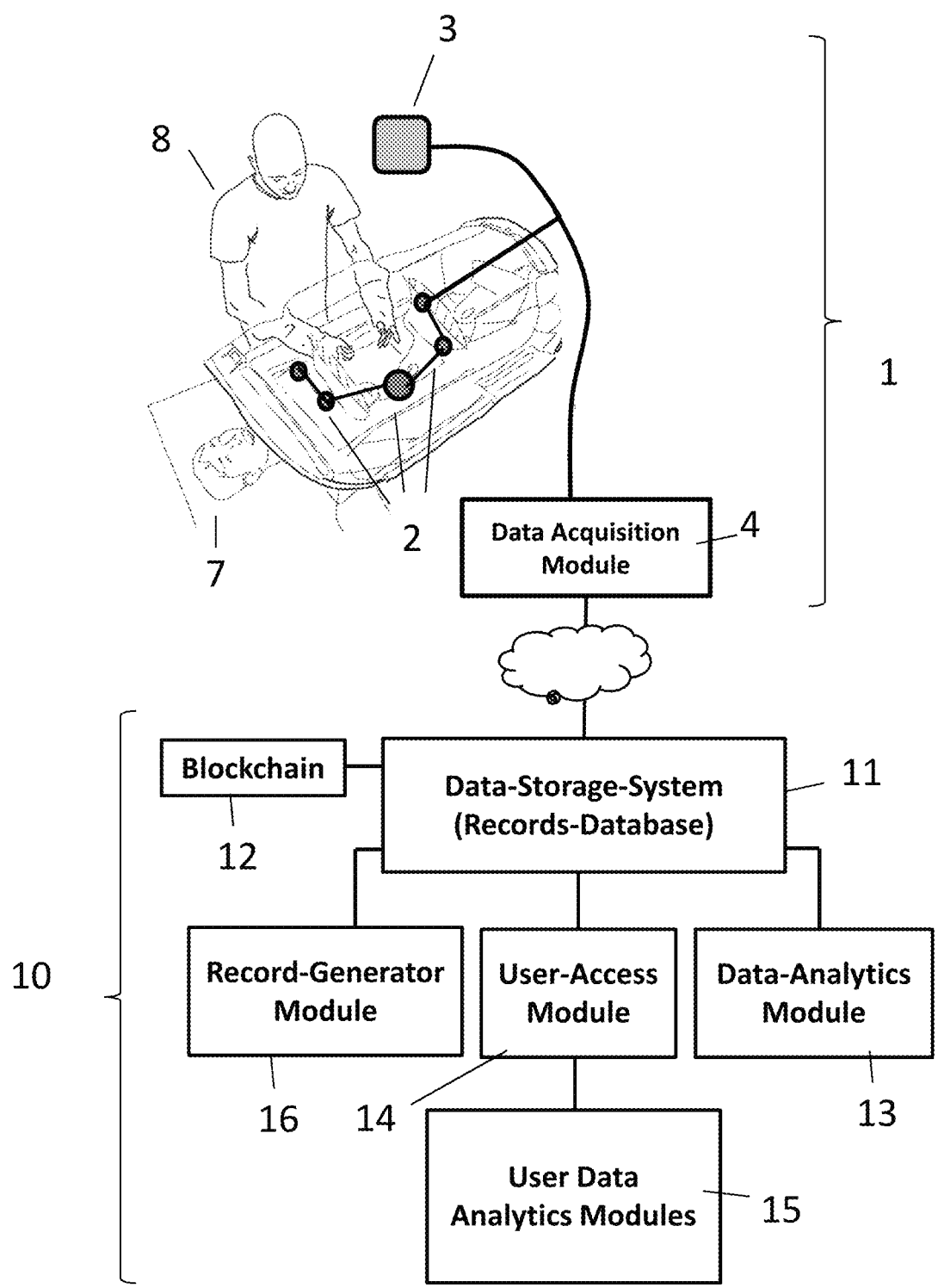
FIG. 2 shows a data-management-system connected with a data-acquisition-system and configured to process and manage data generated during surgical and other medical procedures.

FIG. 2 shows a data-management-system 10 connected with a data-acquisition-system 1 and configured to process and manage data generated during surgical and other medical procedures. The data-management-system 10 may include one or more of the following: a data-storage-system 11, one or more blockchain-systems 12, one or more data-analytics-units 13, one or more user-access-modules 14, one or more user-analytics-modules 15, and a record-generatormodule 16. The data-storage-system may include one or more records-databases for storing data received from the data-acquisition-system 1 and from other data-acquisition-systems where other medical-procedures are performed. The blockchain-systems may be configured to render immutable the data in the records-database. The data-analytics-unit may be connected with the records-database and may be configured to process and perform analytics on the data. The user-access-module may allow users (e.g., researchers, hospital administrators, government, etc.) to access the data in the database and to perform studies on the data associated with medical procedures. The users may perform data analytics on the data in the records-database by using the data-analytics-unit connected with records-database or by using user-data-analytics-units 15 (e.g., modules located on user's computer).

Figure 3:
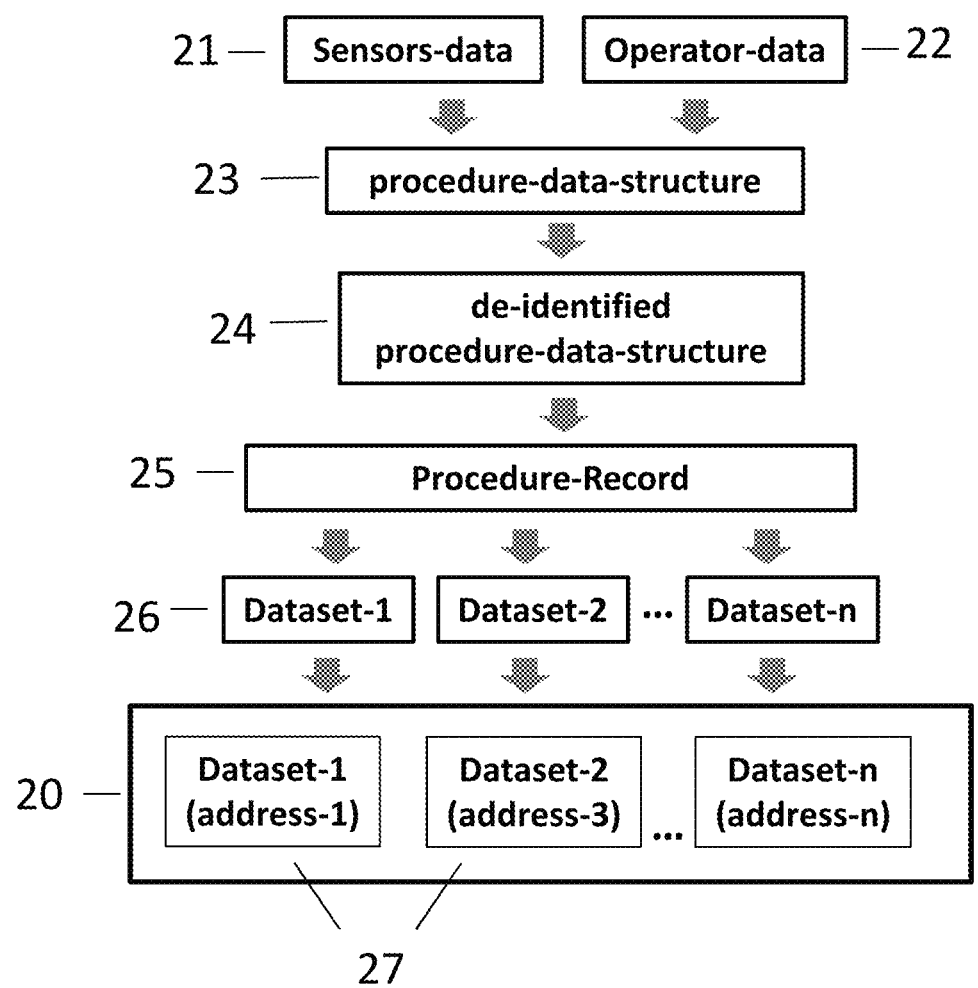
FIG. 3 shows an exemplary embodiment of the data processing performed by the data-management-system in which the blockchain system stores datasets on the blockchain, each of the datasets having a specific address on the blockchain.

The functioning of the data-acquisition-system and data-management-system is explained hereinafter with reference to a certain medical-procedure (e.g., surgery) performed on a certain patient by one or more medical-operators (e.g., surgeons) in a hospital or other facility of a medical service-provider. FIG. 3 shows an exemplary embodiment of the data flow in a data-management-system connected with a data-acquisition-system. The sensors generate sensor-data 21 which is transmitted, intermittently or continuously, to the data-acquisition-module. The medical-operator generates operator-data 22 associated with procedure. The operator-data may include one or more of the following: information about patient identity and medical history, current status of the patient, information regarding the procedure to be performed including steps, purpose, monitoring parameters, patient risk factors, end results, etc. The data-acquisition-system may form a procedure-data-structure 23 which may include sensors-data (e.g., all or part of the data acquired from the sensors during the procedure, which may be processed using standard techniques known in the art such as noise removal, feature extraction, etc.) and the operator-data. The data-acquisition-system may include a de-identification-module configured to remove from the procedure-data-structure all information which may identify the patient thereby forming the de-identified procedure-data-structure 24. The de-identified procedure-data-structure 24 may be sent to the data-management-system 10 where it may be stored (i.e., the entire or part of the procedure-data-structure) in a procedure-record 25 of the records-database 11. The de-identified procedure-data-structure 24 may be sent to the data-management-system 10 via an internet connection, a wireless intranet connection, wired connection, or other data transmission methods known in the art. In an alternative embodiment, the de-identification of the health information is not performed, and patient identity is linked to the data in procedure-data-structure 23.

FIG. 4 shows an exemplary embodiment of a procedure-record 25 for a medical procedure performed on a patient. As seen the procedure-record may include a description of the surgical procedure, patient de-identified information (e.g., age, medical conditions, medical history), sensor data (e.g., intracranial pressure data, blood pressure data), and imaging data (e.g., X-ray images, MRI scans, surgery videos).

The procedure-record 25 may be rendered immutable by a blockchain system. The blockchain system may include a private or a public blockchain. The procedure-record 25 my include one or more datasets 26 (see for example dataset-1, dataset-2, and dataset-n in FIG. 3). The datasets may have substantially the same size (e.g., 100 kB, 1 MB, 10 MB etc.), the size being predetermined so as to be suitable for storing on the blockchain. In the exemplary embodiment shown by FIG. 3 the datasets are stored on the blockchain 20, each of the datasets having a specific address on the blockchain 20 (i.e., address-1, address-2, address-n). For each of the datasets stored on blockchain, a counterpart-dataset (i.e., a copy of the dataset) may be stored on the records-database. The blockchain-addresses may be stored in the databases. The datasets stored on blockchain may be rendered immutable and their integrity may be ensured by the blockchain technology. The datasets may be accessed (for example, via a download) by using their address but the datasets cannot be altered. The data-management-system may further store links to the blockchain-addresses and/or the datasets on a website associated with the database so as to allow others (e.g., healthcare administrators, researchers, physicians, surgeons, etc.) to view and access specific datasets and procedure-records. The data integrity of the counterpart-datasets may be periodically evaluated by comparing the counterpart-datasets (stored on the records-database, not on blockchain) with the corresponding blockchain stored dataset and the dataset hash value.

Figure 5:
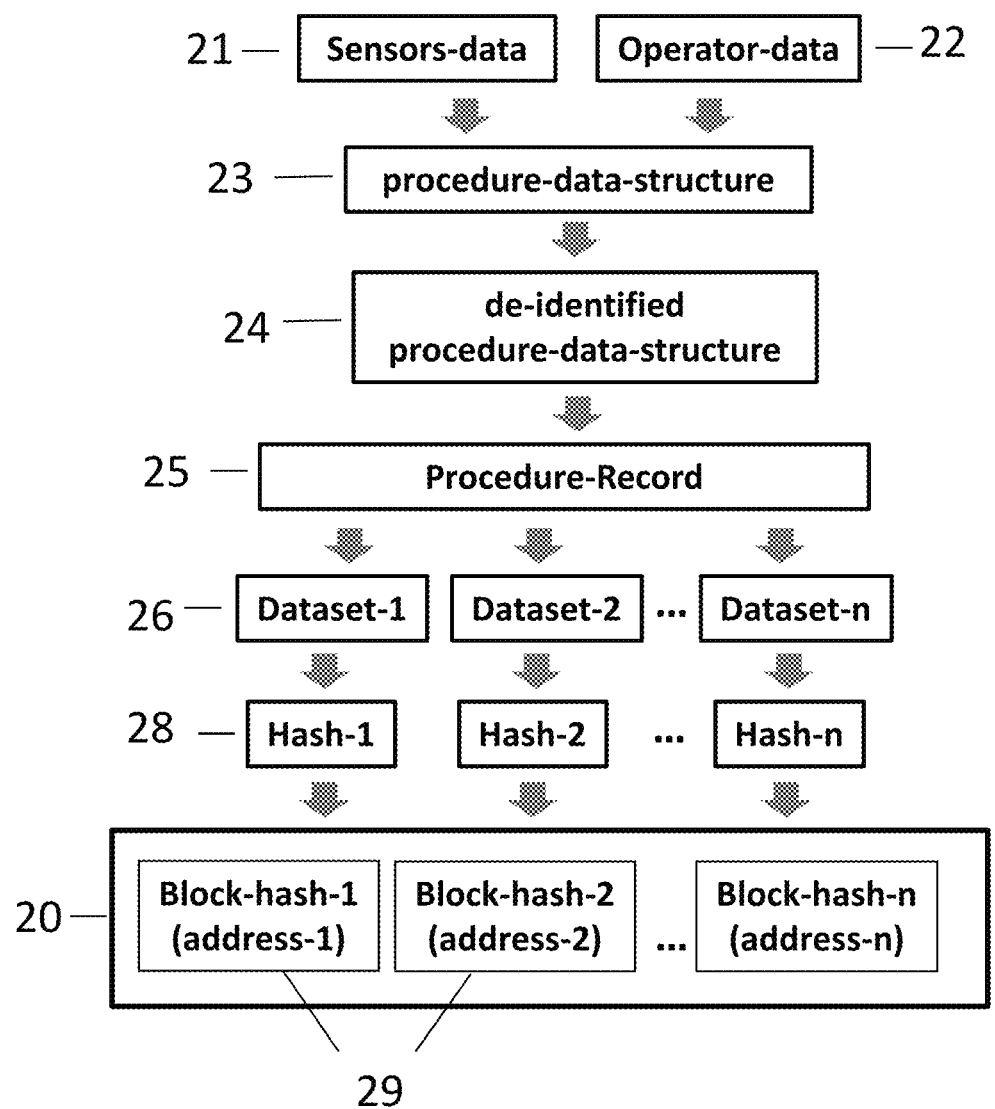
FIG. 5 shows an exemplary embodiment of the data processing performed by the data-management-system including a hash-module using a hash-function to calculate hash values of datasets, wherein the hash values are stored on a blockchain system.

FIG. 5 shows an exemplary embodiment of the data-management-system in which the hashes of the datasets are stored on the blockchain. In this embodiment the data-management-system may include a hash-module. The hash-module is configured to employ a hash-function to calculate hash values 28 for the datasets 26 of the procedure-record (see dataset-1, dataset-2, dataset-n). The data-management-system may store the dataset hash values on the blockchain as block-hash-values 29, wherein each of the block-hash-values 29 has a specific address on the blockchain 20. The blockchain-system may further store the blockchain addresses of the dataset-hash-values in the database and as associated with their corresponding procedure-record 25. For example, consider dataset-1 and block-hash-1 of the procedure-record-1 stored on the blockchain at time-1. The blockchain address-1 (where block-hash-1 is located on the blockchain) is stored on the database and is associated with dataset-1 of the procedure-record.

The blockchain-system may be configured to verify the integrity of any one of the datasets by calculating a hash of the dataset and comparing the calculated hash with the corresponding block-hash stored on the blockchain. For example, once the dataset-1 is stored in the database and its corresponding block-hash-1 is stored on the blockchain, the blockchain-system may verify the integrity of dataset-1 (at a verification-time which is after time-1) by calculating the hash value of dataset-1 (as stored in the database at the verification-time) and comparing the calculated hash with the block-hash-1 stored on the blockchain. If the calculated hash is different from block-hash-1, then dataset-1 has been corrupted or altered. If the calculated hash is identical with block-hash-1, then dataset-1 has not been altered. This way the blockchain-system is able to periodically verify the integrity of the datasets in the procedure-records and to keep the procedure-records immutable.

Figure 6:
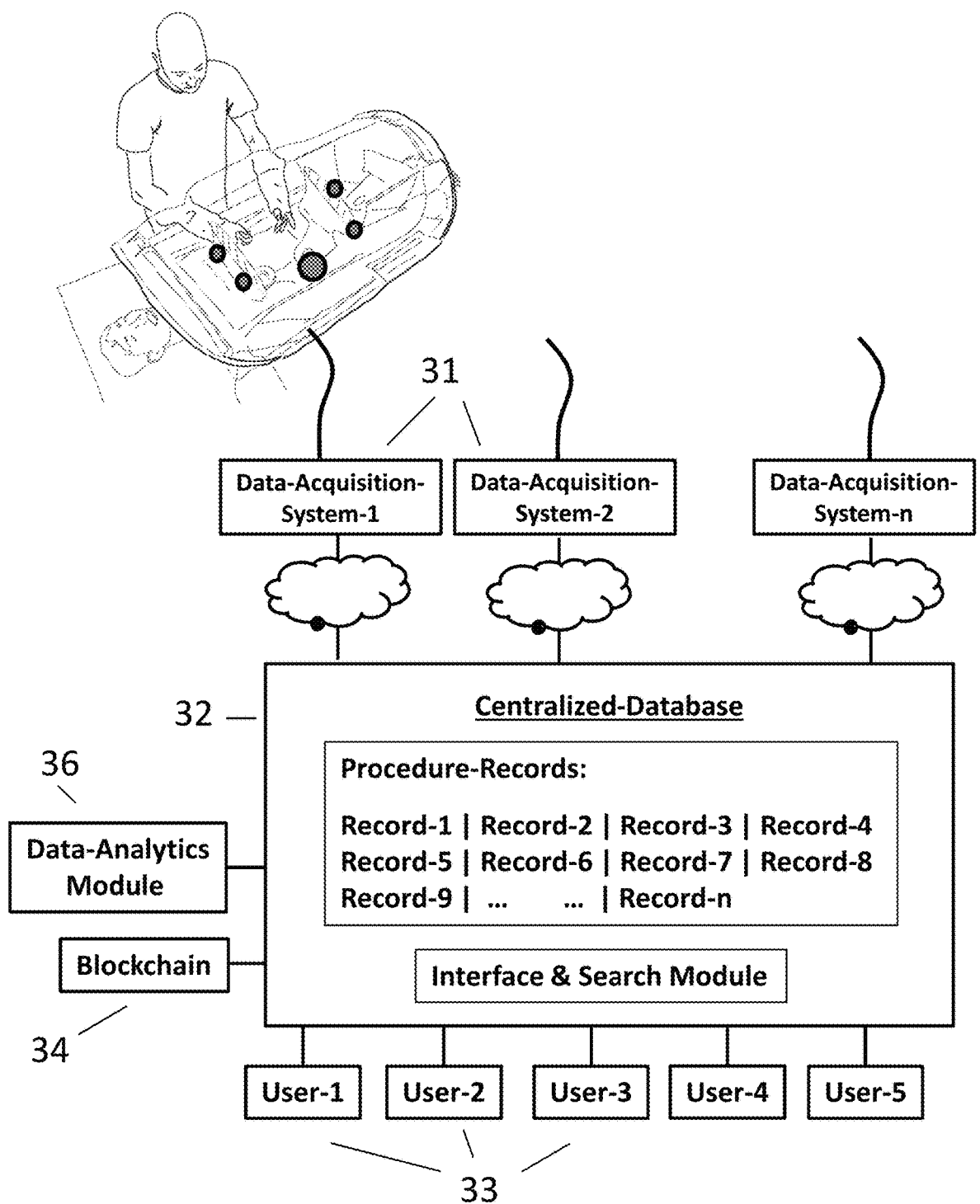
FIG. 6 shows an exemplary embodiment of a data-management-system connected with a plurality of data-acquisition-systems, each of the data-acquisition-systems being configured to acquire sensor and imaging data generated during a specific medical procedure performed on a certain patient.

FIG. 6 shows an exemplary embodiment of a data-management-system connected with a plurality of data-acquisition-systems 31. Each of the data-acquisition-systems 31 is configured to acquire sensor and imaging data generated during a specific medical procedure performed on a certain patient. For example, data-acquisition-system-1 may be used to acquire data during a medical-procedure-1 performed on patient-1 by operator-1 of a service-provider-1; whereas data-acquisition-system-2 may be used to acquire data during a medical-procedure-2 performed on patient-2 (which is different from patient-1) by operator-2 (different from operator-1) of a service-provider-2 (which may be different form service-provider-1). Each of the data-acquisition-systems 31 may perform the operations described above with reference to FIG. 3 or the operations described with reference to FIG. 5, thereby forming their own de-identified procedure-data-structure. For example, data-acquisition-system-1 may form a de identified procedure-data-structure-1 whereas data-acquisition-system-2 may form de-identified procedure-data-structure-2.

The data-management-system may include a centralized-database 32 configured to receive the procedure-data-structure generated by various data-acquisition-systems and to form procedure-records (see e.g., Record-1, Record-2, to Record-n in FIG. 6) corresponding to each of the procedure-data-structure. The data in the centralized-database (e.g., the procedure-records) may be rendered immutable via one or more blockchains 34 by operations such as described above with reference to FIG. 3 or the operations described with reference to FIG. 5.

The centralized-database 32 may be configured to enable a plurality of users 33 (e.g., user-1 to user-5 in FIG. 6) to access the data in the centralized-database. The users may be researchers, scientists and other professionals which may use the procedure-records to perform various studies. The centralized-database may be made accessible to the public or to a specific group of people. The centralized-database may be connected with or may include an interface and search module enabling users to search, select, view, and/or download data in the database. The centralized-database may be connected with a data-analytics-module 36 enabling users to perform data analytics studies on various data. Alternatively, users may be enabled to access data (e.g., download files) and to perform data analytics and other studies via their own data analytics software or other analytics resources.

Figure 7:
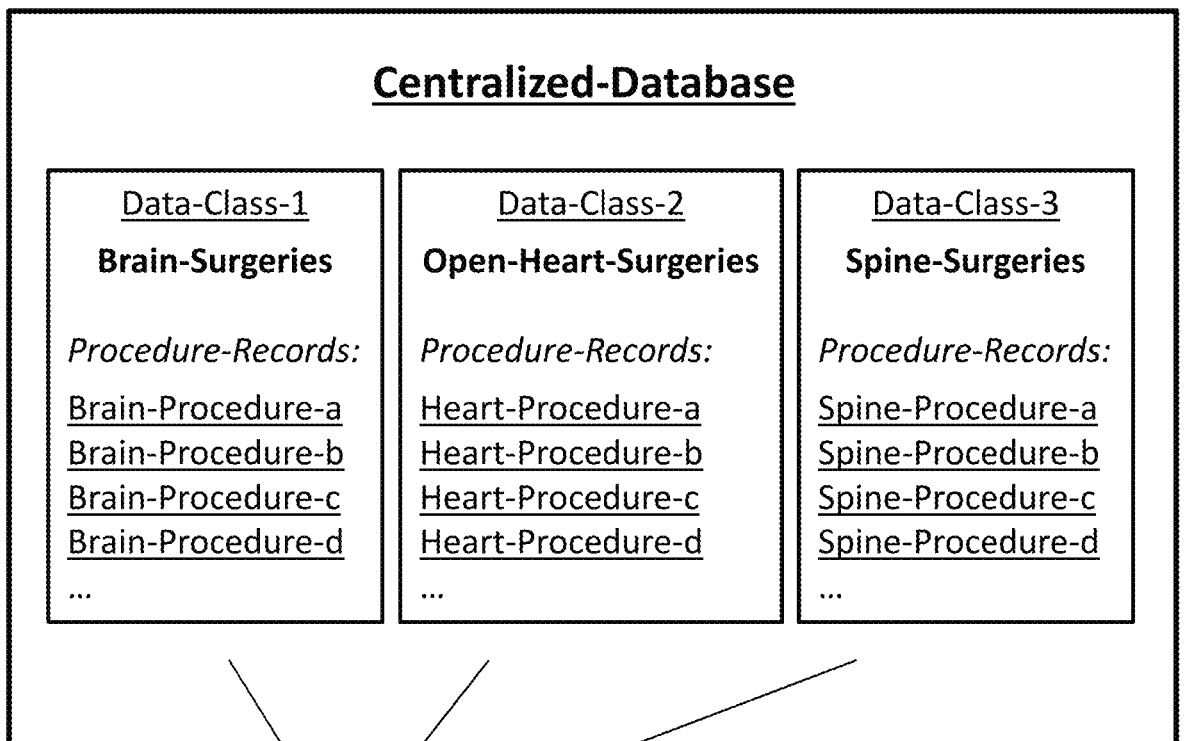
FIG. 7 shows an exemplary embodiment of a centralized-database in which the procedure-records are classified, via a classification-module, and grouped in data-classes by the type of medical procedure.

The data-management-system may include a classification-module for categorizing and forming classes/groups of medical-procedures into one or more data-classes. The procedure-records stored by the centralized-database may be categorized/classified function of various classification-parameters of the procedure-record and/or the corresponding medical procedure, such as: the type of medical procedure; patient's age; procedure's date; type of equipment used during the medical-procedure; physiological parameters recorded by sensors during the medical procedure (patient's blood pressure, cranial pressure, body temperature, heart rate, etc.). FIG. 7 shows an exemplary embodiment of a centralized-database 32 in which the procedure-records are classified and grouped in data-classes 35 (e.g., data-class-1, data-class-2, data-class-3) by the type of medical procedure. These classes may be inferred or automatically determined from the sensor data, user input, or a combination thereof. For example, data-class-1 may include the procedure-records for brain-surgeries, data-class-2 may include the procedure-records for open heart surgery, and data-class-3 may include the procedure-records for spine surgery. The grouping of procedures in classes may be performed so that the classes are the optimal "data units" for performing analytics and studies. For example, a person who wants to study a specific occurrence during open heart surgery is most likely to want to consider the data in the procedure-records for open heart surgery. The data in a data-class may be analyzed via data analytics procedures (e.g. data-mining, machine learning, artificial Intelligence) with the purpose of finding "correlations" between various medical-parameters, patient-parameters and medical-outcomes.

This classification may be performed via a wide variety of techniques known to those skilled in the art. In a non-limiting embodiment, the classification may be done with Natural Language Processing techniques. For example, topic modeling may be applied to procedure records and may be used to create a 'topic' frequency vector for each procedure note to compare notes across procedures and cluster procedures with similar 'topic' distributions into groups to facilitate search. Term frequency vectors extracted per note may be combined with similarity calculations across the corpus of notes, vector similarity computation techniques such as cosine similarity or Jaccard similarity may be used, whereas the vectors may contain weighted term frequencies such as but not limited to Term Frequency-Inverse Document Frequency (TF-IDF) or may contain unweighted term frequencies.

Named Entity Recognition algorithms may be used to identify drugs and diseases in the notes and classify the notes based on such entities. Machine translation algorithms may be used in case of notes in different languages. Supervised learning classification algorithms may cause these and other features to automate assignment of the procedure into categories that are relevant for the users of the database (for example, procedure names commonly accepted in the medical profession, or ICD 10 may be used to categorize based on diagnoses or disease codes). Combinations of terms such as bigrams, trigrams, or any type of n-gram may be used as features for a classifier. Word embeddings or sentence embeddings may also be used as features. Classification algorithms may include but are not limited to standard techniques known in the art, such as: decision trees, k-nearest-neighbors, naïve-bayes, support vector machine, neural networks, random forests, or ensemble methods, to name a few. The procedure data may not necessarily be in textual format.

In another embodiment the notes may be spoken to by a physician during a procedure and transformed into a textual note via a speech to text translation algorithm. Features such as intonations, breathing rate, rate of speech, etc. may be used as well to identify procedures that were complex or where unexpected events occurred during a procedure.

The classification of the procedure may not necessarily require textual data; in another embodiment, a video of the surgical area may be used instead (or still images from a camera) in order to classify the type of procedure, complications, blood loss, or any other adverse events, as well as to identify standard steps common to most procedures within a procedure category. Such data may be used to train a surgical robot in both standard flows of procedures as well as remedies in cases of complications. In an embodiment the images or video could include timestamps. The classification of the procedure may include video, photographic, sound, text, sensor data, as well as any combination thereof.

Figure 8:
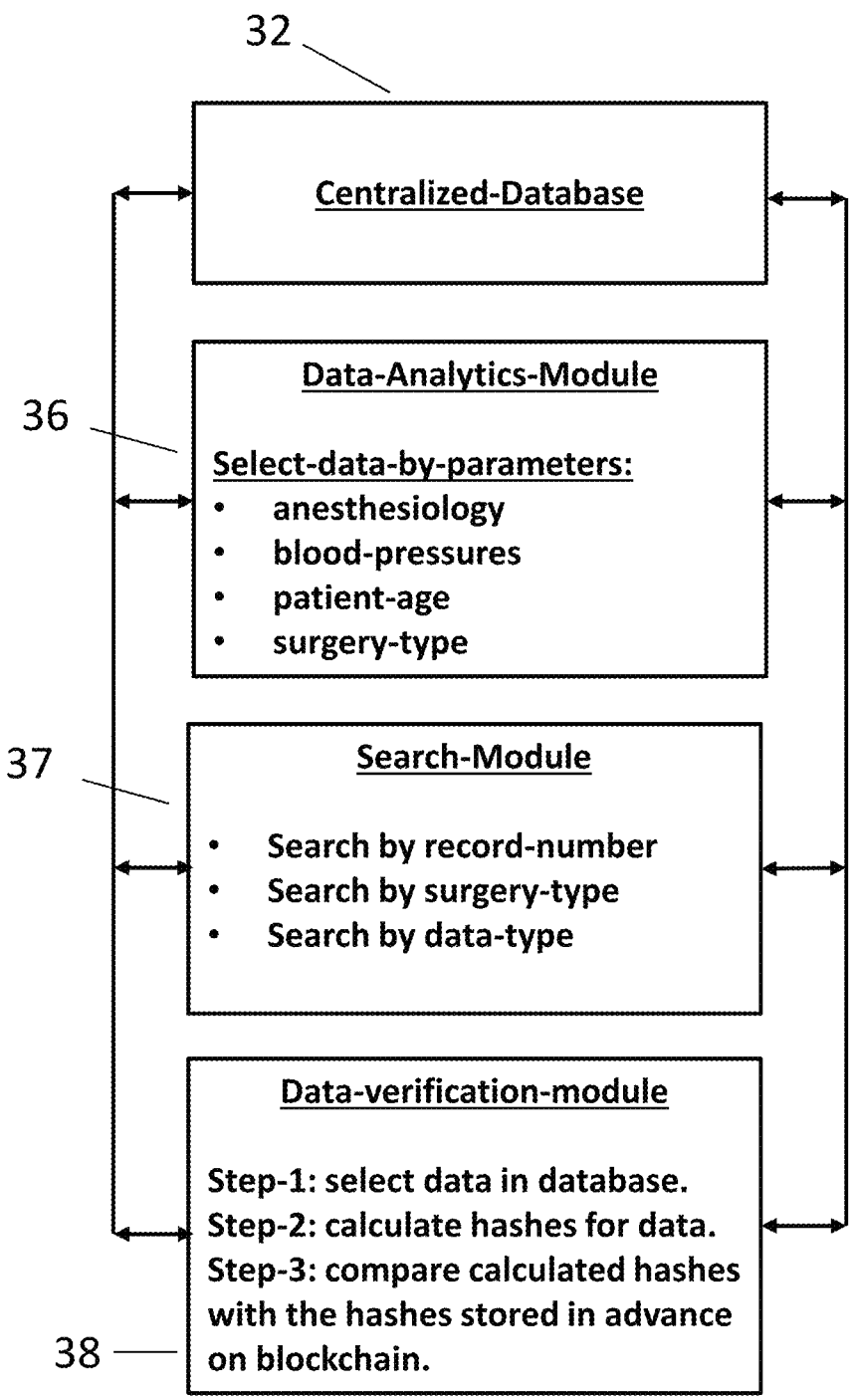
FIG. 8 shows an exemplary embodiment of a data-management-system including a centralized-database, connected with a data-analytics-module, a search interface, and a data-verification-module.

FIG. 8 shows an exemplary embodiment of a data-management-system including a centralized-database 32, such as in FIG. 6, connected with a data-analytics-module 36, a search module 37, and a data-verification-module 38. The data-analytics-module 36 may include tools for selecting specific data in the procedure-records by various parameters, such as anesthiology related data, patient's blood pressure, patient's age, type of procedure, etc. The data-analytics-module may include tools enabling users to perform certain analytics operations and protocols (e.g., data-mining, machine learning, text analysis, AI-based decision support systems) on the selected data. The data-analytics-unit may be configured to find "correlations" between various medical-parameters, patient-parameters, and medical-outcomes. The search-module 37 may enable users to search data in the procedure-records according to parameters such as record-number, surgery-type, data-type, patient's current medical conditions, medical history, etc.

The data-verification-module 38 may enable users to select certain data (e.g., set of procedure-records) and to validate the integrity of the data, i.e., to ensure that the selected data was not altered or corrupted. If the selected data is directly stored on blockchain, then the integrity of the data is ensured by the integrity of the blockchain. If counterparts of the data are stored on the blockchain then the data integrity of the counterpart-datasets may be evaluated periodically (or at specific times) by comparing the counterpart-datasets (stored on the records-database, not on blockchain) with the corresponding blockchain stored dataset. This latter embodiment is particularly useful in situations where the block size of the blockchain implementation is small and cannot fit a full medical procedure record/surgical record dataset; in this case, a hash value calculated based on the dataset is stored on the blockchain together with a location to the dataset, whereas the actual medical procedure record dataset/surgical procedure data can be stored off the blockchain, in a separate database system. Users wishing to verify the integrity of the data can compare the hash value of the dataset per the blockchain entry with the hash value of the dataset stored off the blockchain; should these not match, the dataset is rejected as not the genuine entry.

If the selected data includes datasets for which the integrity is ensured via cryptographic hashes stored on a blockchain, then the data-verification-module may enable users to validate the selected data by calculating the hashes of the datasets and comparing the calculated hashes with the corresponding hashes stored on the blockchain. Please note that the calculated hashes are calculated at the time when the verification is performed (i.e., verification-time) whereas the hashes stored on blockchain were calculated and stored at a blockchain-storing-time which may be essentially the time when the procedure-record was formed.

Figure 9:
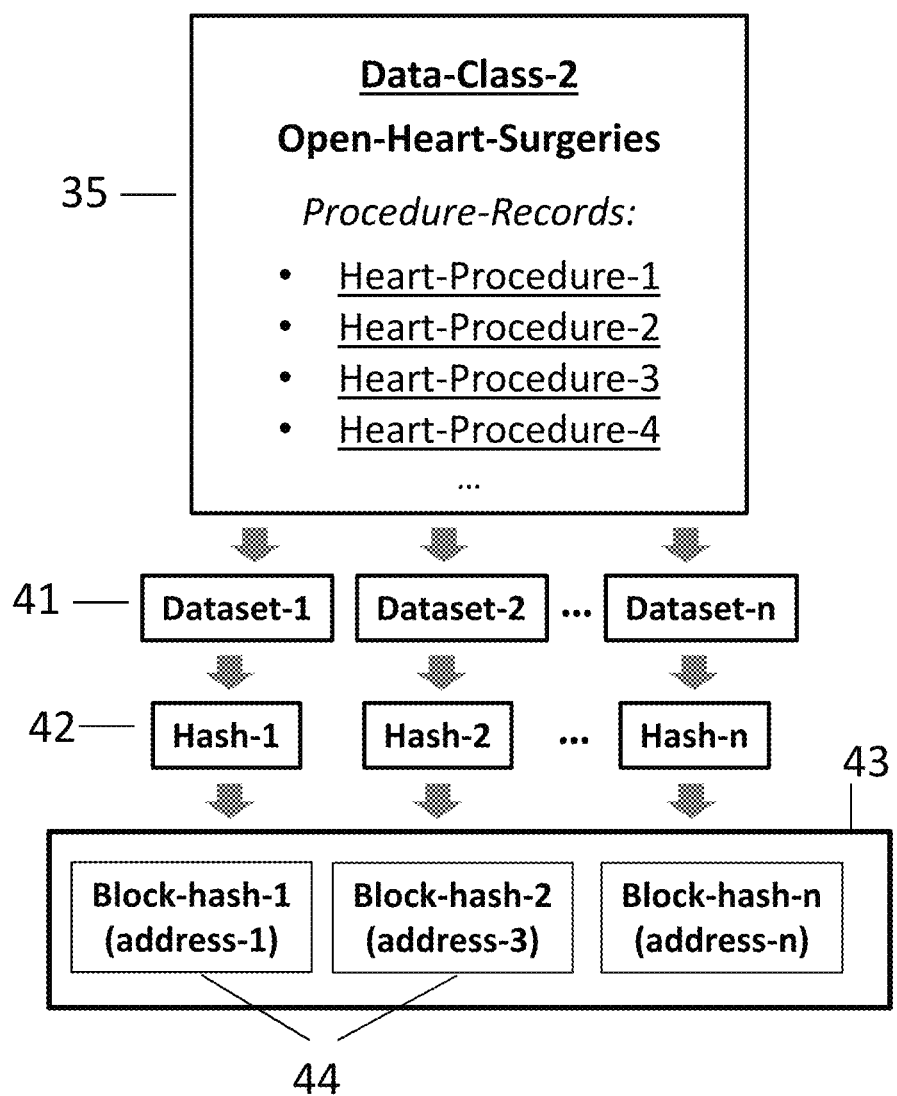
FIG. 9 shows an exemplary embodiment of a method for securing the integrity of the data in the databases, wherein the data in the data-classes is grouped and/or organized in a plurality of datasets and a hash is calculated for each of the datasets.

FIG. 9 shows an exemplary embodiment of a method for securing the integrity of the data in the records-database. The data in the data-classes 35 is grouped and/or organized in a plurality of datasets 41 (i.e., dataset-1, dataset-2, . . . dataset-n). Each of the datasets may be secured via the blockchain by calculating a hash 42 for the dataset and storing the hash on the blockchain 43 as a block-hash 44. Alternatively, copies of the datasets may be stored directly on the blockchain. The datasets may have substantially the same size (e.g., 1 MB, or 100 kB), the size being predetermined so as to be suitable for storing on the blockchain.

Data-management-systems such as the one described with reference to FIG. 6 may be difficult to implement because they require that a majority or a large number of service providers (e.g., hospitals, private practices, healthcare companies) agree to have a third party (e.g., administrator of the centralized-database) copy and store their medical data on a system controlled by the third party. Understandably, many healthcare providers are reluctant to give their data to someone else. The data-management-system described below with reference to FIG. 10 circumvents the problem described above, i.e., having data owned by service-providers copied, stored, and managed by someone else.

Figure 10:
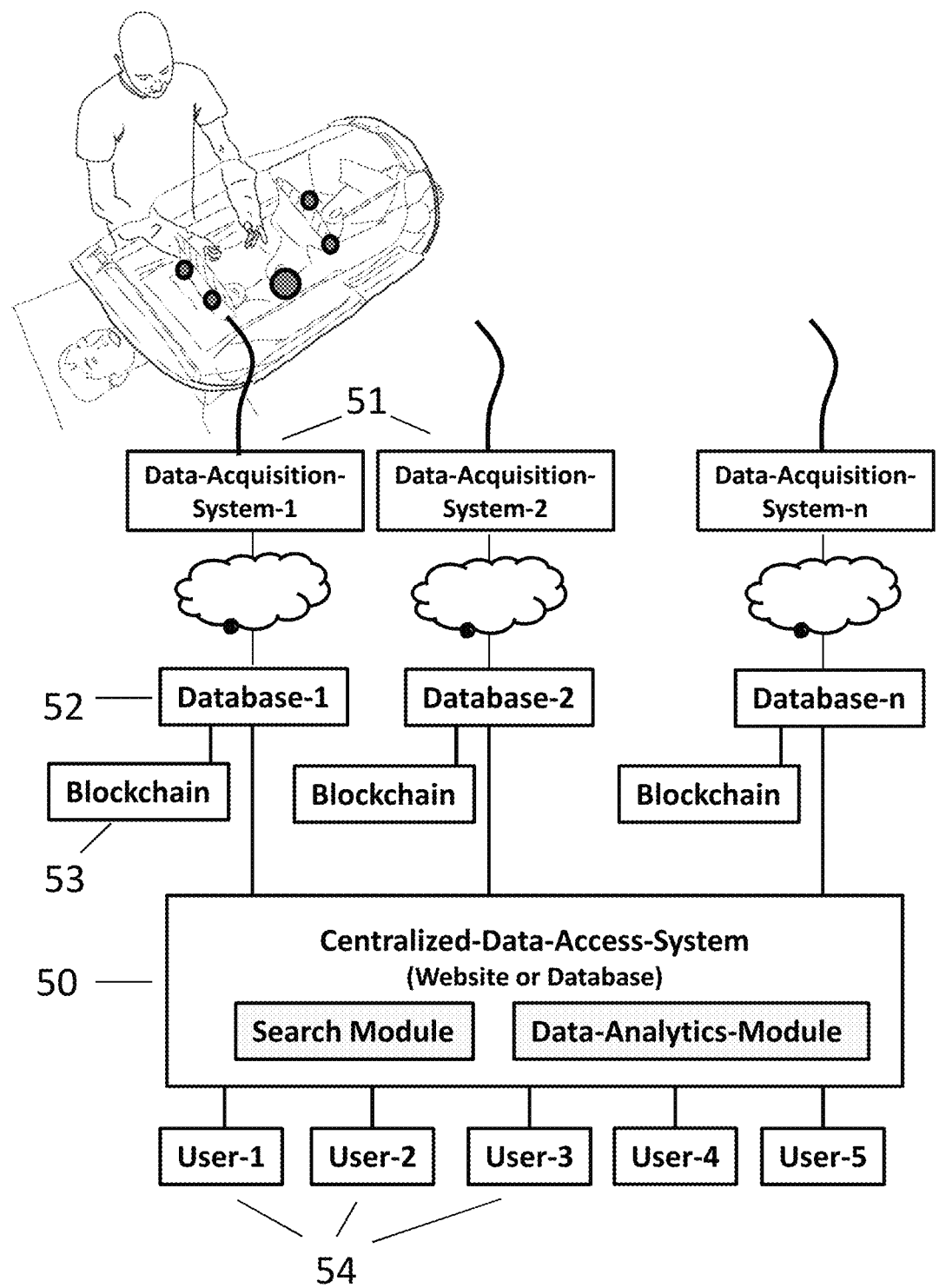
FIG. 10 shows an exemplary embodiment of a data-management-system comprising a centralized-data-access-system connected with a plurality of databases, wherein each of the databases is owned by a different service provider and comprises procedure-records for medical procedures performed by a different service provider.

FIG. 10 shows an exemplary embodiment of a data-management-system connected with a plurality of data-acquisition-systems 51. Each of the data-acquisition-systems 51 is configured to acquire sensor and imaging data generated during a specific medical procedure performed on a certain patient. For example, data-acquisition-system-1 may be used to acquire data during a medical-procedure-1 performed on patient-1 by operator-1 of a service-provider-1; whereas data-acquisition-system-2 may be used to acquire data during a medical-procedure-2 performed on patient-2 (which is different from patient-1) by operator-2 (different from operator-1) of a service-provider-2 (which may be different form service-provider-1). Each of the data-acquisition-systems may perform the operations described above with reference to FIG. 3 or the operations described with reference to FIG. 5, thereby forming their own procedure-data-structures (including de-identified data) which may be stored in databases 52 owned by the service-providers performing the medical procedure.

For example, a procedure-record-1 including de-identified procedure-data-structure acquired during medical-procedure-1 is stored on database-1, wherein database-1 is owned by service-provider-1 (e.g. a specific hospital). Similarly, a procedure-record-2 including de-identified procedure-data-structure acquired during medical-procedure-2 is stored on database-2, wherein database-2 is owned by service-provider-2 (e.g. a specific hospital). Medical-procedures performed by the same service-provider (e.g. another hospital) may be stored in the same database 52.

The data in the databases 52 may be rendered immutable via one or more blockchains 53 by the operations described above with reference to FIG. 3 or the operations described with reference to FIG. 5. The blockchains employed by different databases may be different from each other (i.e. each database uses its own blockchain). Alternatively, all or part of the databases may employ a common blockchain.

The data-management-system may include a centralized-data-access-system 50 which may further include a website and/or a centralized-access-database. The centralized-data-access-system 50 may include a database-access-module configured to connect the centralized-data-access-system 50 with a plurality of databases 52, each of the databases comprising a plurality of procedure-records. The centralized-data-access-system is configured to enable users 54 (e.g., user-1 to user-5 in FIG. 10) to access the data in the databases 52 (e.g., database-1 to database-n). The centralized-data-access-system may enable users 54 to perform specific studies and data analytics on the all or some of the data in the databases 52. For instance, auditors may verify the integrity of the database system by comparing the hash of its record with a corresponding hash at the appropriate address on the blockchain. Databases 52 may be owned and managed by different service-providers (e.g., different healthcare companies, different hospital systems, different provider offices, etc.). The centralized-data-access-system may be owned and managed by a party (e.g., company or non-profit institution) who is legally bound to keep the data securely for the benefit of the public and the owners of the databases 52.

Different datasets in the databases may be assigned different permission-levels indicating the conditions in which a user can access the data-file and the specific operations a user can perform on a data-file. For example, a permission level for a certain data-file may prescribe that the data-file cannot be download from the database but may be used in analytics studies (e.g., analytics performed in the database with analytic-tools owned by the database owner) and the user can see the results of the study. Each user may have certain permission-level with respect to a data-file in a certain database. For example, user-1 may be permitted to perform certain analytics-operations on some data-files in the database-n owned by hospital-n and to receive the results of the analytics-operations; user-1 may be allowed to see the data-files but may not be allowed to download the files from the database-n; user-2 may only have audit access, i.e., to compare hash values of records with existing records on the blockchain but may not actually see the contents of the datasets used to create the hash values.; other users may have full access. Editing a record would require creation of a new record with its own separate address pointer on the blockchain, address pointer to the record being updated, address pointer to the external database system (if applicable), and hash value. Variations thereof may be envisaged by those skilled in the art.

The centralized-data-access-system may include one or more computer servers including one or more processors and one or more memories (memory modules, database systems, cloud storage devices, etc.). The computer servers may include connection-ports configured to send and receive information to/from the databases 52 and the users 54 via network connections and/or the internet. The centralized-data-access-system may act as the interface between users 54 and databases 52. The centralized-data-access-system may include a search-module enabling users 54 to search data in the databases 52. The centralized-data-access-system may include a data-analytics-unit enabling users to select data and perform various analytics operations and studies on the data in the databases 52. The centralized-data-access-system may include one or more websites enabling users to access and use the search-module and the data-analytics-module.

Figure 11:
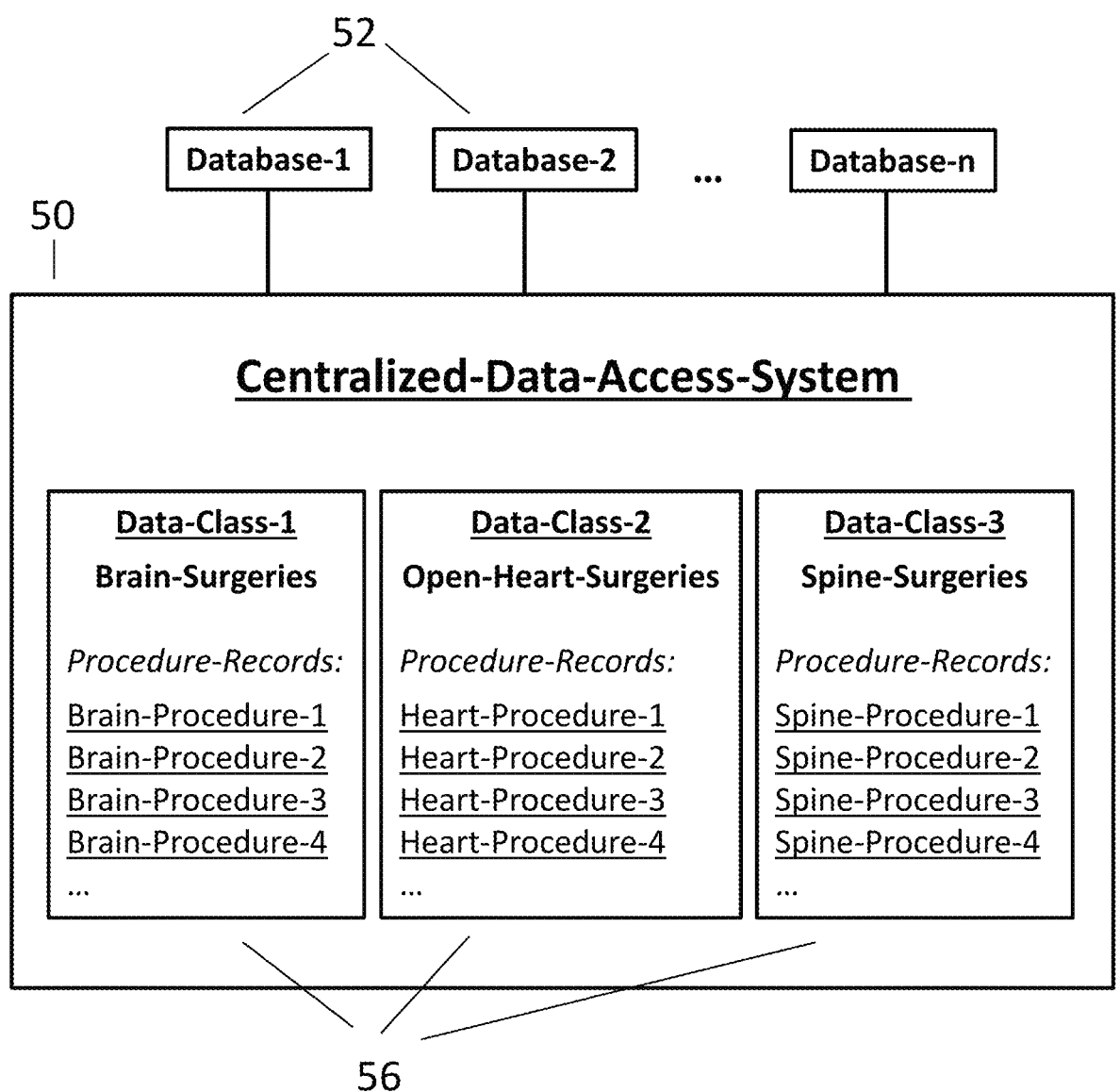
FIG. 11 shows an exemplary embodiment of an interface of the centralized-data-access-system showing several data-classes, wherein each of the data-classes may include pointers to data files and procedure-records stored in various databases.

The centralized-data-access-system may include a classification-module for categorizing and forming classes/groups of medical-procedures into one or more data-classes. FIG. 11 shows an exemplary embodiment of an interface of the centralized-data-access-system 50 displaying several data-classes 56 formed by the classification-module. Each of the data-classes 56 may include pointers (or links) to data files and procedure-records stored in various databases 52. The links/pointers may point to procedure-records and/or files stored on different databases 52 owned by different service-providers. For example, data-class-1 may include all procedure-records for which the medical procedure is a brain surgery. Data-class-1 may include a procedure-record (e.g. Brain-Procedure-a) which is stored in database-2 owned by service-provider-2, a procedure-record (e.g. Brain-Procedure-b) which is stored in database-1 owned by service-provider-1, and a procedure-record (e.g. Brain-Procedure-c) which is stored in database-5 owned by service-provider-5. The centralized-data-access-system 50 is connected and provides access to various procedure-records in databases 52, wherein each of the databases is owned by a different service-provider (e.g. hospital, private practice, university).

The data-classes may be formed as described with reference to FIG. 7. A data-class may include all the procedure-records (in all databases, i.e., database-1 to database-n) for which a classification parameter has a certain parameter-value. The classification parameters may include, but not be limited to: the type of medical procedure; patient's age; procedure's date; type of equipment used during the medical-procedure; physiological parameters recorded by sensors during the medical procedure (patient's blood pressure, cranial pressure, body temperature, heart rate, etc.). For example, the classification-parameter for the data-classes shown in FIG. 11 is the type of medical procedure (e.g., brain surgery, open heart surgery, and spine surgery).

The classification-parameters may be chosen so that the formed data-classes are the optimal "data units" for performing analytics and scientific studies. For example, a person who wants to study a specific occurrence during open heart surgery is most likely to want to consider the data in the procedure-records for open heart surgery. The data in a data-class may be analyzed via data analytics procedures (e.g., data-mining, machine learning, text analytics, etc.) with the purpose of finding relationships between various medical-parameters, patient-parameters and medical-outcomes.

Figure 12:
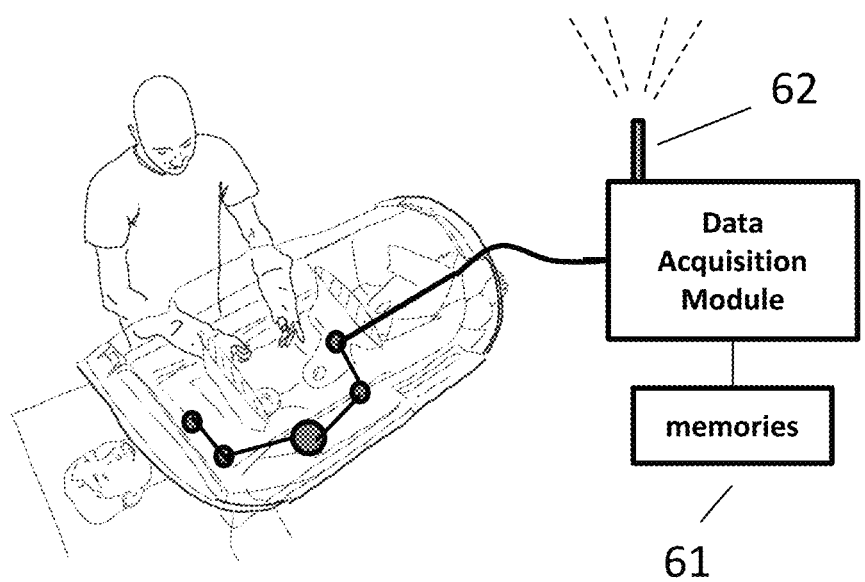
FIG. 12 shows an exemplary embodiment of a data-acquisition-system connected with a data-management-system, wherein the data-acquisition-system is part of a portable surgical system configured to be used in environments other than operating rooms, such as: in the field, outdoors, tents, cottages, residential rooms, etc.

FIG. 12 shows an exemplary embodiment of a data-acquisition-system connected with a data-management-system, wherein the data-acquisition-system is configured to be included in a portable surgical system 60 such as the one disclosed in the international patent application PCT/US2017/042266 titled "Ultraportable System for Intraoperative Isolation and Regulation of Surgical Site Environments" and filed on Jul. 14, 2017 by D. Teodorescu et al. The portable surgical system may be used to perform surgery in environments other than operating rooms, such as in the field, outdoors, tents, cottages, residential rooms, etc. When used in field applications (e.g., outdoors, remote areas) the data-acquisition-system most often cannot be connected with databases in real time, such as the ones described with reference to FIGS. 2 to 11, because in the field there may be no available internet or network connections (neither cable connections nor Wi-Fi connections). For in the field applications, the data-acquisition-system may include one or more memories 61 and/or a satellite-connection-device 62.

The memories are configured to store the data generated by the sensors, by the imaging system, and/or data input by the operators. The memories may store the data while there is no connection with the data-management-system. Once a connection with the data-management-system is established (e.g., the data-acquisition-system is connected to internet via a cable, Wi-Fi, or by a satellite connection, or some other means) then the data in the memories may be sent to the databases of the data-management-system (see e.g., databases described with reference to FIGS. 2, 6, 7, 10, and 11) and stored on the databases in a corresponding procedure-record hashed, and have a corresponding block-hash created.

Especially for the in the field applications, satellite connections are useful because they provide a way to transmit data to databases from the field (e.g., remote areas). The satellite-connection-device may be configured to send (via a satellite connection) to the data-management-system the data generated by the sensors, by the imaging system, and/or data input by the operators. This way data generated during medical procedures performed in the field may be sent to the databases of the data-management-system even in the absence of cable or Wi-Fi connections to the internet.

The above embodiments presented in this disclosure merely serve as exemplary embodiments and it will be apparent to those skilled in the art that various modifications and variations can be made in the present invention without departing from the spirit or scope of the invention. The terminology used herein is for the purpose of describing particular embodiments only and is not intended to be limiting of the present disclosure. The inventions herein may be embodied in many different forms and should not be construed as limited to the exemplary embodiments set forth herein. Rather, these exemplary embodiments are provided so that this disclosure is thorough, and will fully convey the scope of the invention to those skilled in the art.

LIST OF REFERENCES

[1]. Intraoperative Monitoring; Dr. Liji Thomas, MD, News Medical Net (Feb. 27, 2019)
[2]. "Recommendations for standards of monitoring during anesthesia and recovery 2015", Association of Anesthetists of Great Britain and Ireland

[3]. "Guidance Regarding Methods for De-identification of Protected Health Information in Accordance with the Health Insurance Portability and Accountability Act (HIPAA) Privacy Rule" published by the U.S. Department of Health and Human Services.

[4]. International patent application number PCT/US2017/042266 titled "Ultraportable System for Intraoperative Isolation and Regulation of Surgical Site Environments" and filed on Jul. 14, 2017 by Teodorescu et. al.

What is claimed is:

1. A data-management-system for managing data acquired during medical procedures, the data-management-system comprising:
   a centralized-database, including one or more memory devices, comprising one or more procedure-records; wherein each of the procedure-records comprises data acquired by a data-acquisition-system during a medical procedure performed on a specific patient;
   a user-access-module configured to enable users to access data in the centralized-database; and
   a search-module configured to enable users to perform searches on data in the centralized-database;
   wherein the centralized-database is connected with a plurality of data-acquisition-systems and wherein each data-acquisition-system, of the plurality of data-acquisition-systems, comprises:
      one or more sensors attached to a patient and monitoring one or more physiological parameters of the patient;
      an operator-input-module configured to receive information from an operator regarding the medical procedure to be performed and the patient;
      a data-acquisition-module configured to receive data from the sensors and to form a procedure-data-structure comprising the data from the sensors;
      a de-identification-module configured to form a de-identified-procedure-data-structure;
      a record-generating-module configured to receive the de-identified-procedure-data-structures and to form, for each of the de-identified-procedure-data-structures, a corresponding procedure-record comprising the de-identified-procedure-data-structure;
      a display module configured to display at least one of the one or more physiological parameters of the patient; and
      a blockchain system, including one or more hardware processors, configured to store datasets comprised by the procedure-record or to store hashes of datasets comprised by the procedure-record.

2. The data-management-system of claim 1, wherein each of the procedure-records in the centralized-database comprises one or more datasets, and wherein each of the datasets, or copies of the datasets, are stored on the blockchain system at a dataset-address.

3. The data-management-system of claim 1, further comprising a hash-module configured to employ a hash-function to calculate hashes for one or more datasets comprised by the procedure-records;
   wherein the blockchain system is configured to store each of the hashes on a blockchain thereby forming a block-hash for each of the hashes;
   wherein each of the block-hashes has a block-hash-address; and
   wherein each block-hash-addresses of the block-hashes is stored in the centralized-database.

4. The data-management-system of claim 3, further comprising a data-verification-module configured to verify, for each dataset of the datasets of the procedure-records, an integrity of the dataset by calculating a hash of the dataset and comparing the calculated hash with the corresponding block-hash previously stored for the dataset on the blockchain.

5. The data-management-system of claim 1, further comprising a classification-module configured to select a classification-parameter and to form a plurality of data-classes corresponding to the classification-parameter; and
   wherein each of the data-classes comprises one or more procedure-records.

6. The data-management-system of claim 5, wherein the data in each of the data-classes is partitioned into a plurality of datasets;
   wherein the data-management-system further comprises a hash-module configured to employ a hash-function to calculate hashes for the datasets;
   wherein the blockchain system is configured to store each of the hashes on a blockchain thereby forming a block-hash for each of the hashes;
   wherein each of the block-hashes has a block-hash-address; and
   wherein each block-hash-addresses is stored in the centralized-database.

7. The data-management-system of claim 5, wherein the data-acquisition-system further comprises one or more imaging-devices configured to acquire video data and photographic data of a surgical field;
   wherein the data-acquisition-system further comprises a sound-recording-device configured to record sound data during medical procedure;
   wherein the one or more procedure-records in the centralized-database comprise the video data, the photographic data, and the sound data; and
   wherein the classification-module is configured to classify the one or more procedure-records to one or more of: video data, photographic data, sound data, text, and sensor data.

8. The data-management-system of claim 1, further comprising a data-analytics-module, including the one or more hardware processors, configured to enable users to perform data-analytics and scientific studies on the data in the centralized-database.

9. The data-management-system of claim 1, wherein the data-acquisition-system is part of a portable-surgical-system configured to be used for performing surgical procedures in one or more of: in a field, outdoors, in tents, cottages, residential rooms, and environments other than hospital operating rooms.

10. A data-management-system for managing data acquired during medical procedures, the data-management-system comprising a centralized-data-access-system further comprising:
    a database-access-module configured to connect the centralized-data-access-system with a plurality of databases, each of the databases comprising one or more procedure-records;
    wherein each of the databases is connected to a plurality of data-acquisition-systems, and each of the data-acquisition-systems comprises:
       one or more sensors attached to a patient and monitoring one or more physiological parameters of the patient;
       an operator-input-module configured to receive information from an operator regarding a medical procedure to be performed and the patient;

a data-acquisition-module configured to receive physiological data from the sensors and to form a procedure-data-structure comprising the physiological data;

a de-identification-module configured to form a de-identified-procedure-data-structure;

wherein each of the procedure-records comprises the information in a de-identified-procedure-data-structure corresponding to a medical procedure performed on a patient;

a blockchain system, including one or more hardware processors, configured to store datasets comprised by the one or more procedure-records or to store hashes of datasets comprised by the one or more procedure-records;

an user-interface-module configured to enable one or more users to access data-files in the databases;

a display module configured to display at least one of the one or more physiological parameters of the patient; and a search-module configured to enable the users to search data in the databases.

11. The data-management-system of claim 10, wherein each database of the plurality of databases is owned by a different healthcare service-provider.

12. The data-management-system of claim 10, further comprising a hash-module configured to employ a hash-function to calculate hashes for one or more datasets comprised by the one or more procedure-records;

wherein the blockchain system is configured to store each of the hashes on a blockchain thereby forming a block-hash for each of the hashes; and wherein each of the block-hashes has a block-hash-address.

13. The data-management-system of claim 12, further comprising a data-verification-module, including the one or more hardware processors, configured to verify, for each of the datasets of the one or more procedure-records, an integrity of the dataset by calculating a hash of the dataset and comparing the calculated hash with the corresponding block-hash previously stored for the dataset on the blockchain.

14. The data-management-system of claim 10, wherein the centralized-data-access-system further comprises a classification module configured to select a classification-parameter and to form a plurality of data-classes corresponding to the classification-parameter; and wherein each of the data-classes comprises the one or more procedure-records.

15. The data-management-system of claim 14, wherein the data in each of the data-classes is partitioned into a plurality of datasets;

wherein the data-management-system further comprises a hash-module configured to employ a hash-function to calculate hashes for the datasets;

wherein the blockchain system is configured to store each of the hashes on a blockchain thereby forming a block-hash for each of the hashes and the datasets; and wherein each of the block-hashes has a block-hash-address.

16. The data-management-system of claim 14, wherein each data-acquisition-system of the data-acquisition-systems further comprises one or more imaging-devices configured to acquire video data and photographic data of a surgical field;

wherein the data-acquisition-system further comprises a sound-recording-device configured to record sound data during medical procedure;

wherein the one or more procedure-records in a centralized-database comprise the video data, the photographic data, and the sound data; and wherein the classification module is configured to classify the one or more procedure-records to one or more of: video data, photographic data, sound data, text, and sensor data.

17. The data-management-system of claim 10, further comprising a data-analytics-module configured to enable users to perform data-analytics and scientific studies on data in each database of the plurality of databases.

18. The data-management-system of claim 10, wherein each data-acquisition-system is part of a portable-surgical-system configured to be used for performing surgical procedures in one or more of: in a field, outdoors, tents, cottages, residential rooms, and environments other than operating rooms.

19. A method by using a data-management-system, the method comprising:

receiving sensors-data from one or more sensors attached to a patient during a medical procedure performed by an operator, the sensors monitoring one or more physiological parameters of the patient;

receiving, from the operator, operator-data regarding the medical procedure;

forming a procedure-data-structure comprising the sensors-data and the operator-data;

forming a de-identified-procedure-data-structure;

using the de-identified-procedure-data-structure to form a procedure-record for the medical procedure and storing the procedure-record on a database of a service-provider;

partitioning the procedure-record into one or more datasets;

displaying at least one of the one or more physiological parameters of the patient;

calculating a block-hash for each of the datasets by using a hash-function; and storing each of the block-hashes on a blockchain.

20. The method of claim 19, further comprising:

receiving from a user a search request to select a set of procedure-records, out of the procedure-records stored in a set of databases; and performing a data-analytics operation on the set of procedure-records.

21. The method of claim 20, further comprising:

receiving from a user a classification request according to one or more classification-parameters; and classifying the procedure-records stored in the set of databases, according to the classification-parameters, into one or more procedure-record-classes.

22. The method of claim 19, wherein the medical procedure is performed by a portable-surgical-system in one or more of: in a field, outdoors, tents, cottages, residential rooms, and environments other than operating rooms.

23. The method of claim 19, further comprising: using one or more named entity recognition algorithms to classify the procedure-records in a centralized-database and to identify drugs and diseases in the procedure-records of the centralized-database.

24. The method of claim 19, further comprising: using one or more supervised learning classification algorithms to automatically classify the procedure-records into categories and procedure-record-classes.

\* \* \* \* \*